United States Patent
Ni et al.

[11] Patent Number: 6,052,176
[45] Date of Patent: Apr. 18, 2000

[54] PROCESSING CHAMBER WITH OPTICAL WINDOW CLEANED USING PROCESS GAS

[75] Inventors: Tuqiang Ni; Wenli Collison, both of Fremont, Calif.

[73] Assignee: Lam Research Corporation, Fremont, Calif.

[21] Appl. No.: 09/282,519

[22] Filed: Mar. 31, 1999

[51] Int. Cl.$^7$ .............................. G01B 11/00; G02B 7/00
[52] U.S. Cl. .............................. 356/72; 359/509; 216/60; 438/16; 356/381
[58] Field of Search .............................. 356/72, 317, 318, 356/381, 382; 216/60, 85; 438/14, 16; 359/509

[56] References Cited

U.S. PATENT DOCUMENTS

| | | | |
|---|---|---|---|
| 4,469,713 | 9/1984 | Schwiecker et al. | 356/381 |
| 4,582,431 | 4/1986 | Cole | 356/382 |
| 4,816,294 | 3/1989 | Tsuo et al. | 427/582 |
| 5,807,761 | 9/1998 | Coronel et al. | 438/14 |

*Primary Examiner*—F. L. Evans
*Attorney, Agent, or Firm*—Hickman Stephens Coleman & Hughes

[57] ABSTRACT

An apparatus is provided including a semiconductor processing chamber enclosed by a plurality of walls. Also included is a source of process gas that is required for processing a wafer within the processing chamber. Mounted on one of the walls of the processing chamber is a window. An inlet is positioned adjacent to the window and remains in communication with the processing chamber. The inlet is further coupled to the source of process gas to channel the process gas into the processing chamber for both preventing the deposition of byproducts on the window and further processing the wafer within the processing chamber. In another embodiment, a source of light, an analysis mechanism, and an optical transmission medium are provided. Such optical transmission medium is coupled between the source of light and the analysis mechanism and is further aligned with the window for directing light into the processing chamber and analyzing the wafer within the processing chamber. The window is configured to reflect the light received from the optical transmission medium at an angle so as to not interfere with light reflected from the wafer within the processing chamber.

32 Claims, 4 Drawing Sheets

6,052,176

PROCESSING CHAMBER WITH OPTICAL WINDOW CLEANED USING PROCESS GAS

FIELD OF THE INVENTION

The present invention relates generally to semiconductor processing chamber windows and, more particularly, to a semiconductor processing chamber window with an adjacent process gas inlet that effectively prevents the deposition of byproducts on the window while avoiding the alteration of a process gas composition within the processing chamber.

BACKGROUND OF THE INVENTION

In semiconductor fabrication, various processes are monitored by collecting data and analyzing conditions within a semiconductor processing chamber. This is traditionally carried out using a window mounted, for example, on a side wall of the processing chamber. Prior Art FIG. 1 shows one example of a window 10 mounted on a side wall of a conventional processing chamber 12. As shown, the window 10 is recessed with respect to the side wall of the processing chamber 12.

While various processes are carried out within the processing chamber 12, byproducts in the form of polymer precursors and residue tend to accumulate on the window 10. This interferes with the collection of data and analysis of conditions within the processing chamber 12. To overcome this difficulty, a source of inert gas 14 is commonly used to channel an inert gas in front of the window 10 for removing the byproducts. In prior art processing chambers 12, Helium (He) is commonly used to clean the window 10.

While Helium is effective in removing polymer precursors from the window 10, difficulties do arise which result from use of such inert gas. For example, Helium tends to at least partially affect the process within the process chamber 12 by diluting and/or altering the gas composition within the processing chamber 12. As such, a flow rate of the Helium is kept to a minimum to prevent a large volume of the gas from being injected into the process chamber 12. In the end, the reduced flow rate of Helium is only partially effective in removing the byproducts from the window 10. To compensate for this deficiency, an inboard end of the recessed area has a conventional O-ring 13 to reduce exposure of the window 10 to the byproducts. Such O-ring 13, however, prevents the use of equipment commonly employed for analyzing wafers within the process chamber.

There is thus a need for a semiconductor processing chamber with optical window that effectively prevents the deposition of byproducts on the window while avoiding the alteration of the process gas composition within the processing chamber and allowing use of equipment to analyze wafers within the process chamber.

As mentioned earlier, the processes within the processing chamber are monitored by collecting data and analyzing conditions. Examples of equipment necessary for such collection and analysis include a lamp, a spectrometer, an optical fiber, and a lens. In use, the optical fiber has a first end aligned with the window with the lens positioned therebetween. A second end of the optical fiber is bifurcated for coupling to both the lamp and the spectrometer.

During operation, the lamp and the spectrometer work together to monitor a process such as deposition, etching, or cleaning by any one of the known optical endpoint detection methods. In one such method, light is reflected off of the wafer and thereafter viewed with the spectrometer. The spectrometer may be connected to a photodetector that converts light from the spectrometer to an electrical signal which is in turn amplified and monitored by a computer to determine a process endpoint or collecting other information.

A complication arises due to the need for directing the light and viewing the reflected light through a single window. In particular, some of the directed light reflects back from the window and tends to interfere with the ability of the spectrometer to receive the light reflected from the wafer within the processing chamber. This reflected light, or noise, prevents the spectrometer and the associated photodetector from delivering an electrical signal that is truly indicative of the light reflected from the wafer within the processing chamber.

There is thus a need for a semiconductor processing chamber that effectively employs a single window to direct light into the processing chamber and receive reflected light without noise for analysis purposes.

DISCLOSURE OF THE INVENTION

The present invention includes a semiconductor processing chamber enclosed by a plurality of walls. Also included is a source of process gas that is required for processing a wafer within the processing chamber. Mounted on one of the walls of the processing chamber is a window. An inlet is positioned adjacent to the window and remains in communication with the processing chamber. The inlet is further coupled to the source of process gas to channel the process gas into the processing chamber for both preventing the deposition of byproducts on the window and further processing the wafer within the processing chamber.

Yet another embodiment of the present invention includes a source of light, an analysis mechanism, and an optical transmission medium. Such optical transmission medium is coupled between the source of light and the analysis mechanism and is further aligned with the window for directing light into the processing chamber and analyzing the interior space of the processing chamber. In the present embodiment, the window is configured to reflect the light received from the optical transmission medium at an angle so as to not interfere with light reflected from within the processing chamber. The window thus allows the analysis mechanism to receive the light reflected from within the processing chamber without interference or noise.

These and other advantages of the present invention will become apparent upon reading the following detailed description and studying the various figures of the drawings.

BRIEF DESCRIPTION OF THE DRAWINGS

The accompanying drawings, which are incorporated in and constitute part of this specification, illustrate exemplary embodiments of the invention and together with the description serve to explain the principles of the invention.

Prior Art

DETAILED DESCRIPTION OF THE PREFERRED EMBODIMENTS

Reference will now be made to the present preferred embodiments of the invention, examples of which are illustrated in the accompanying drawings.

Figure 1:
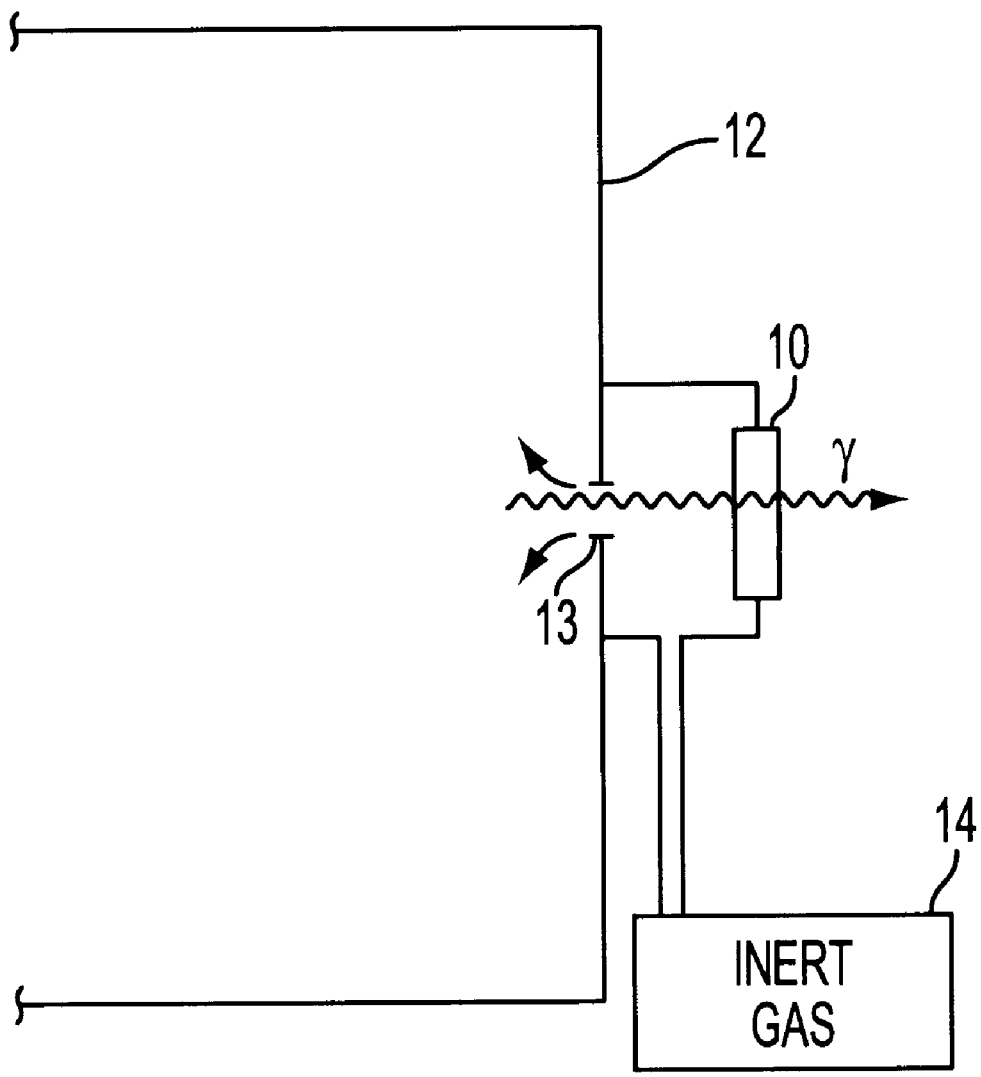
FIG. 1 is a cross-sectional view of a semiconductor processing chamber of the prior art.
Figure 2:
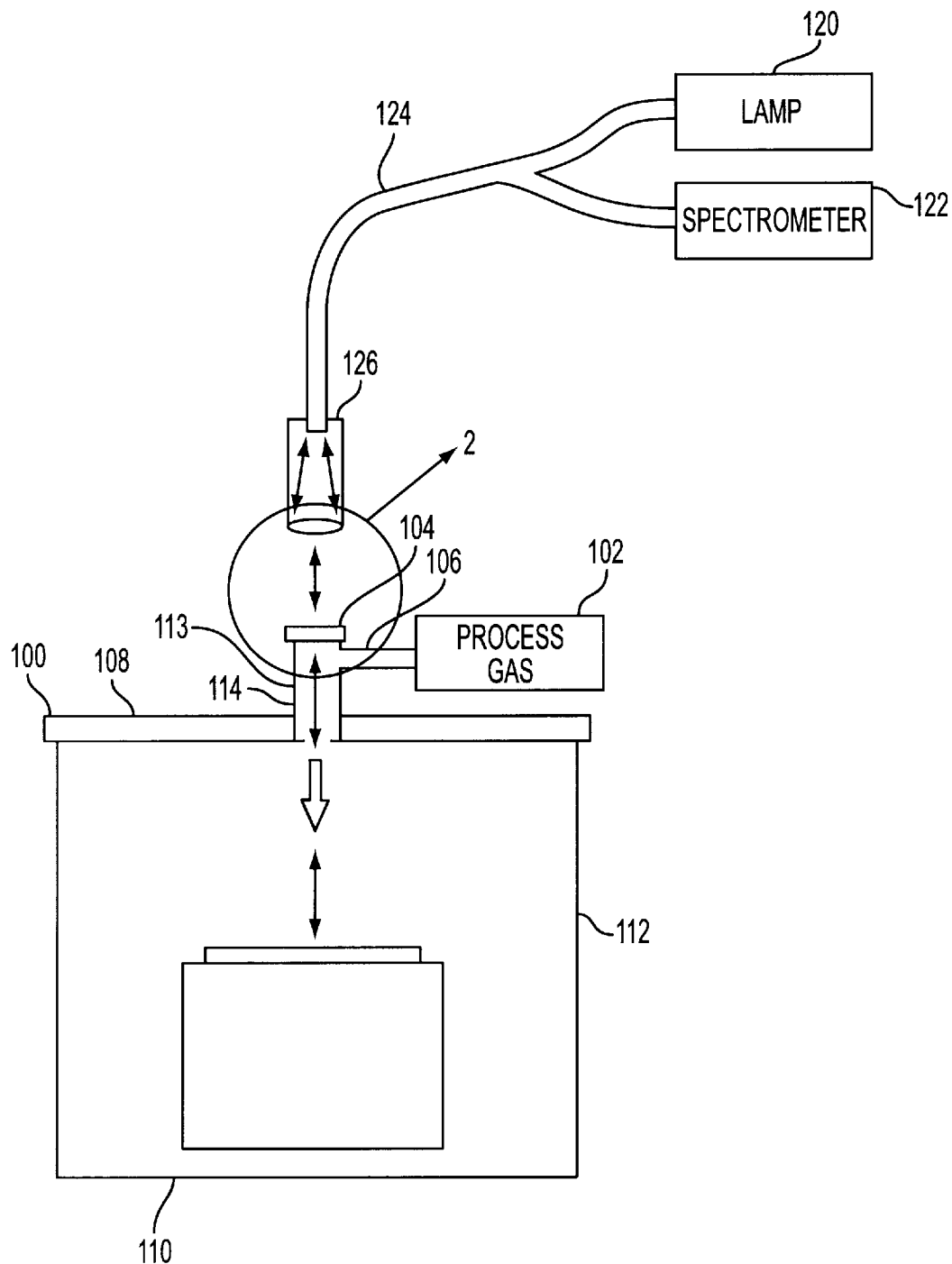
FIG. 2 is a cross-sectional view of a semiconductor processing chamber of one embodiment of the present invention wherein process gas is channeled into the processing chamber adjacent to the window for the purpose of removing byproducts therefrom.
Figure 3:
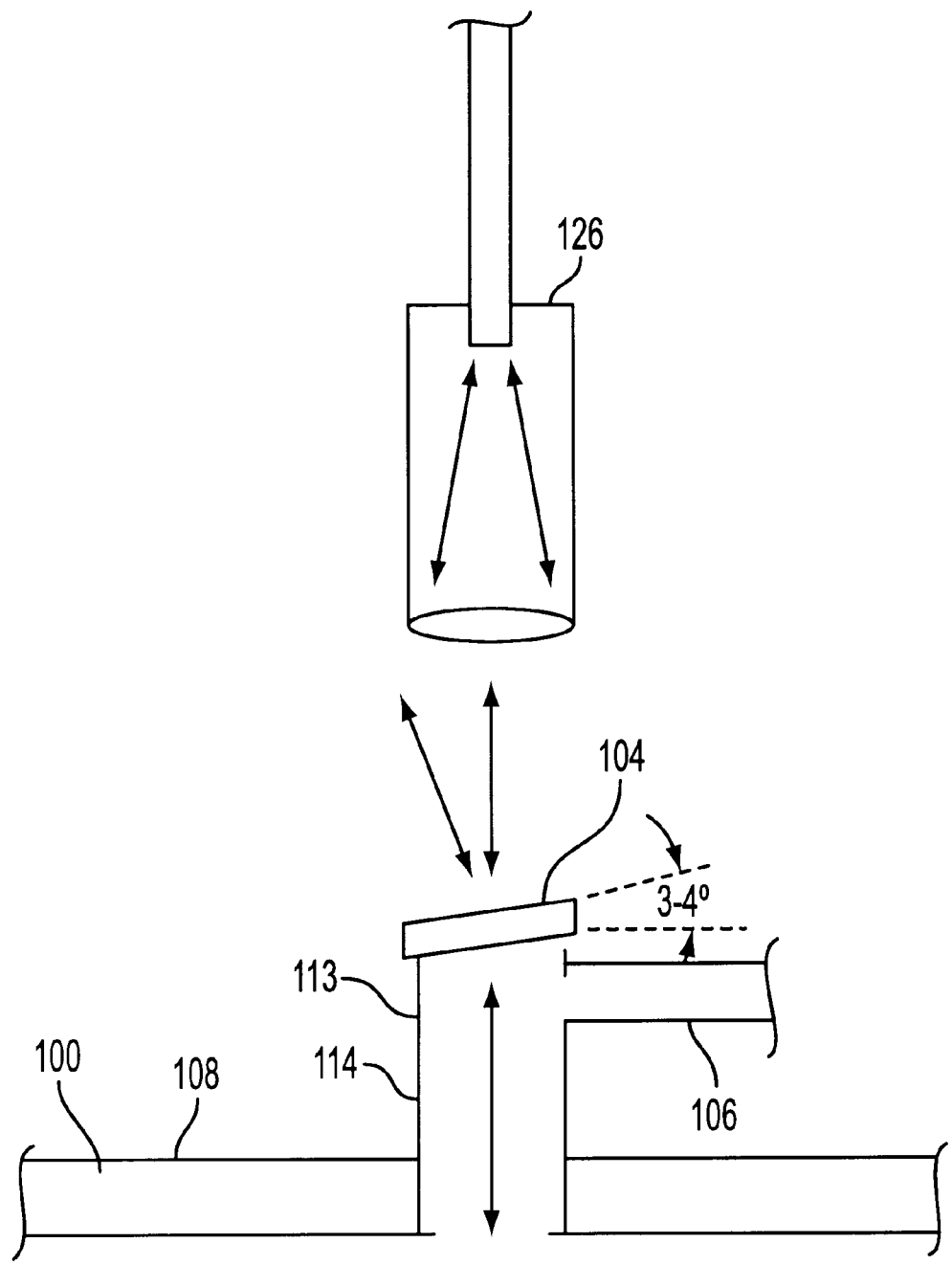
FIG. 3 is a close-up cross-sectional view of the encircled area of FIG. 2 showing the details of the window and other related components of the present invention.
Figure 4:
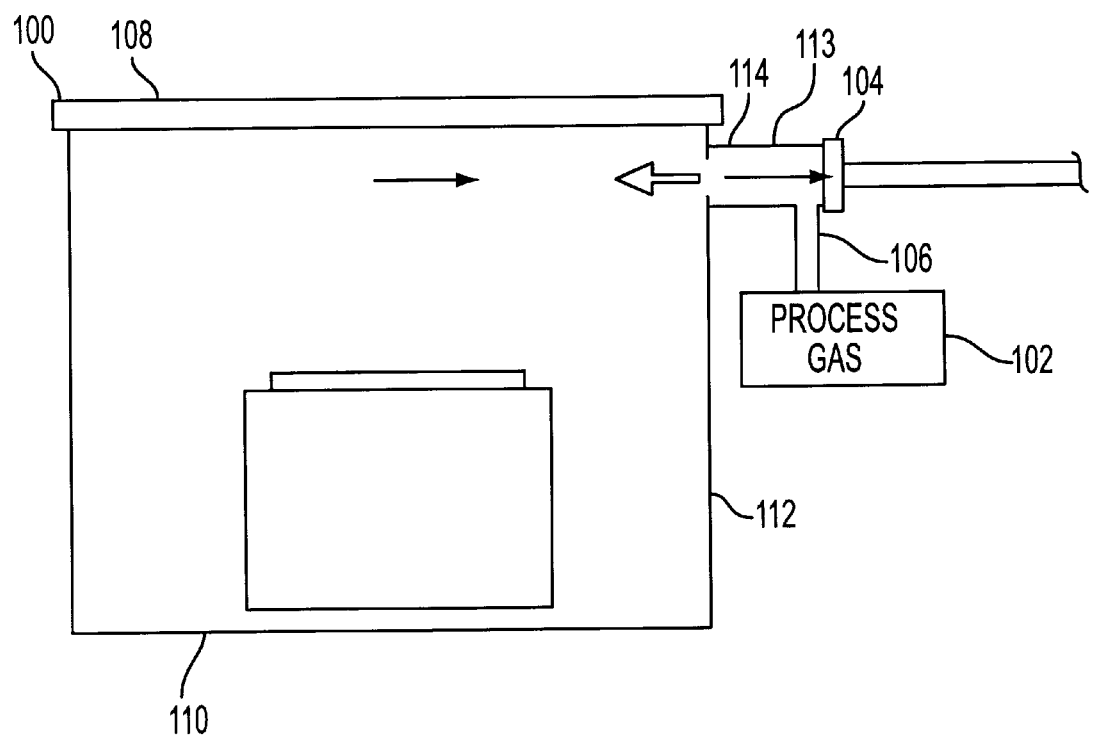
FIG. 4 is a cross-sectional of a semiconductor processing chamber of another embodiment of the present invention wherein the window is positioned on a side wall of the processing chamber.

FIG. 1 illustrates the prior art. With reference to FIGS. 2–4, the present invention includes a semiconductor processing chamber 100, a source of process gas 102, a window 104, and an inlet 106. The processing chamber 100 defines an interior space which is enclosed by a top wall 108, a bottom wall 110, and a plurality of side walls 112. Such processing chamber 100 serves for processing contents, i.e. wafer 110, for the purpose of manufacturing integrated circuits. One step of such processing includes etching the wafer 110. This may be accomplished using any conventional, commonly known techniques.

In order to carry out the etching process, the source of process gas 102 is often required for channeling the process gas into the processing chamber 100. In various embodiments, such process gas, or plasma, may include, but is not limited to $Cl_2+HBr$, $Cl_2$, $CF_4$, $HBr$, $BCl_3$, $SF_6$, $N_2$ or $O_2$. It should be noted, however, that the process gas may take the form of any gas that is used during etching or any other process related to the manufacture of integrated circuits.

In order to allow the collection of data during the semiconductor manufacturing process, a window 104 may be mounted on one of the walls of the processing chamber 100. In one embodiment, the window 104 is situated on the top wall 108 of the processing chamber 100 for the purpose of allowing analysis of the wafer 110 within the processing chamber 100. In another embodiment, the window 104 is situated on the side wall 112 of the processing chamber 100. By positioning the window 104 in such location, one may collect data relating to the process gas and any byproducts produced by the etching of the wafer 110. In still yet another embodiment, a plurality of windows may be mounted on the top wall of the processing chamber for flanking a center of the top wall. For reasons that will soon become apparent, this may be particularly useful during some data collection and analysis techniques. In the foregoing embodiments, the collected data and analysis serve to provide important information relating to the semiconductor manufacturing process.

The inlet 106 is positioned adjacent to the window 104 and remains in communication with the processing chamber 100. The inlet 106 is further coupled to the source of process gas 102 for the purpose of channeling the process gas into the processing chamber 100. This process gas serves to prevent the deposition of polymer precursors on the window 104 which may interfere with the analysis of the contents in the processing chamber 100. Further, by using the process gas as opposed to prior art inert gases, the process gas composition within the processing chamber 100 is unaltered for more effectively processing the wafer 110. It should be noted that the inlet 106 may serve as a primary source of process gas 102 for the processing chamber or, in the alternative, may merely supplement the flow of process gas from a conventional process gas port.

In one embodiment, the window 104 is recessed with respect to the wall of the processing chamber 100 to which the window 104 is mounted. This is accomplished by a substantially right cylindrical prechamber 114 being positioned between the window 104 and the processing chamber 100. As best shown in FIG. 3, the inlet 106 is mounted on a side wall 113 of the prechamber 114 and is positioned adjacent to the window 104.

The specific orientation of the inlet 106 is such that the process gas is directed in a direction perpendicular with respect to an axis of the prechamber 114 and substantially parallel with respect to a lower surface of the window 104. By this structure, the process gas dislodges any byproducts from the lower surface of the window 104 and directs the same through the prechamber 114 and into the processing chamber 100 where the process gas contributes to the processing of the wafer 110. Further, the flow of process gas may be continuous in nature for preventing any byproducts or the like from entering the prechamber 114.

As mentioned earlier, various data may be collected and tests may be performed during semiconductor processing to facilitate the manufacture of the integrated circuits. To aid in such analysis and collection of data, test equipment is provided including a source of light 120, an analysis mechanism 122, an optical transmission medium 124, and a lens 126. As shown in FIG. 2, the optical transmission medium 124 includes an optical fiber having a first end aligned with the window 104 with the lens 126 positioned therebetween. A second end of the optical fiber is bifurcated for coupling to both the source of light 120 and the analysis mechanism 122. In one embodiment, the source of light 120 includes a lamp and the analysis mechanism 122 includes a CCD spectrometer.

In another unillustrated embodiment, the bifurcated optical fiber may be replaced with a pair of separate optical fibers. One of the optical fibers may serve to direct light from the lamp into the processing chamber via a first window. Further, a second one of the optical fibers may be used to collect light reflected from a wafer within the processing chamber via a second window.

During operation, the lamp directs light through the optical fiber for being reflected off of the wafer 110 within the processing chamber 100. In the embodiment wherein the lamp and the analysis mechanism 122 use a single optical fiber, the window 104 may be beveled, or angled, to ensure that any reflected light that does not pass through the window 104 is reflected at angle, as shown in FIG. 3. This prevents such reflected light from being reflected 180° which would direct the light back through the optical fiber and obscure any reflected light from the wafer 110. To accomplish a desired angled reflection, the upper and lower surfaces of lens 126 may be planar, parallel, and form a 3–4° angle with respect to a horizontal. By this structure, the various data may be collected more effectively for endpoint detection, fingerprinting the chamber condition, or any other purpose.

Although only a few embodiments of the present invention have been described in detail herein, it should be understood that the present invention may be embodied in many other specific forms without departing from the spirit or scope of the invention. Therefore, the present examples and embodiments are to be considered as illustrative and not restrictive, and the invention is not to be limited to the details given herein, but may be modified within the scope of the appended claims.

What is claimed is:

1. An apparatus comprising:
   a semiconductor processing chamber enclosed by a plurality of walls;
   a source of process gas that is required for processing contents in the processing chamber;

a window mounted on one of the walls of the processing chamber; and an inlet positioned in communication with the processing chamber, the inlet further coupled to the source of process gas to channel the process gas into the processing chamber for both preventing the deposition of byproducts on the window and further processing the contents in the processing chamber.

2. The apparatus of claim 1 wherein the window is mounted on a side wall of the processing chamber for allowing analysis of the process gas in the processing chamber.

3. The apparatus of claim 1 wherein the window is mounted on a top wall of the processing chamber for allowing analysis of a wafer in the processing chamber.

4. The apparatus of claim 1 wherein the inlet directs the process gas along an axis substantially parallel with a plane in which the window resides.

5. The apparatus of claim 1 wherein the window is recessed with respect to the wall to which the window is mounted.

6. The apparatus of claim 5 wherein the window and the processing chamber are separated by a prechamber.

7. The apparatus of claim 6 wherein the inlet is mounted on a side wall of the prechamber.

8. The apparatus of claim 7 wherein the inlet directs the process gas along an axis substantially parallel with a plane in which the window resides.

9. The apparatus of claim 1 further comprising:

a source of light;

an analysis mechanism;

an optical transmission medium positioned between the source of light and the analysis mechanism and the window for analyzing the contents of the processing chamber;

wherein the window is configured to preclude light received from the source of light to reflect off the window and back into the transmission medium thereby preventing interference with light reflected from the contents of the processing chamber.

10. The apparatus of claim 9 wherein the light is reflected at an angle.

11. The apparatus of claim 9 wherein the window has an upper surface that is angled with respect to a horizontal.

12. The apparatus of claim 9 further including a lens situated between the optical transmission medium and the window for collimating light on a wafer in the processing chamber.

13. The method of claim 1 wherein the process gas is selected from the group of process gases consisting of $Cl_2$+HBr, $Cl_2$, $CF_4$, HBr, $BCl_3$, $SF_6$, $N_2$ and $O_2$.

14. A method comprising:

providing a semiconductor processing chamber enclosed by a plurality of walls with a window mounted on one of the walls of the processing chamber;

providing a source of process gas that is required for processing contents in the processing chamber;

positioning an inlet in communication with the processing chamber;

coupling the inlet to the source of process gas; and channeling the process gas into the processing chamber for both preventing the deposition of byproducts on the window and further processing the contents within the processing chamber.

15. The method of claim 14 wherein the window is mounted on a side wall of the processing chamber for allowing analysis of a gas phase composition in the processing chamber.

16. The method of claim 14 wherein the window is mounted on a top wall of the processing chamber for allowing analysis of a wafer in the processing chamber.

17. The method of claim 14 wherein the inlet directs the process gas along an axis substantially parallel with a plane in which the window resides.

18. The method of claim 14 wherein the window is recessed with respect to the wall to which the window is mounted.

19. The method of claim 18 wherein the window and the processing chamber are separated by a prechamber.

20. The method of claim 19 wherein the inlet is mounted on a side wall of the prechamber.

21. The method of claim 20 wherein the inlet directs the process gas along an axis substantially parallel with a plane in which the window resides.

22. The method of claim 14 further comprising:

providing a source of light and an analysis mechanism;

positioning an optical transmission medium between the source of light and the analysis mechanism and the window for analyzing the contents of the processing chamber;

wherein the window is configured to preclude light received from the source of light to reflect off the window and back into the transmission medium thereby preventing interference with light reflected from the contents of the processing chamber.

23. The method of claim 22 further comprising:

positioning a lens between the optical transmission medium and the window for collimating on the wafer.

24. The method of claim 22 wherein the window reflects the light received from the source of light at an angle.

25. The method of claim 22 wherein the window has an upper surface that is angled with respect to a horizontal.

26. The method of claim 14 wherein the process gas is selected from the group of process gases consisting of $Cl_2$+HBr, $Cl_2$, $CF_4$, HBr, $BCl_3$, $SF_6$, $N_2$ and $O_2$.

27. An apparatus comprising:

a semiconductor processing chamber including an interior space enclosed by a plurality of walls;

a window mounted on a top one of the walls of the processing chamber;

a source of light;

an analysis mechanism;

an optical transmission medium positioned between the source of light and the analysis mechanism and the window for directing light into the processing chamber and analyzing the interior space of the processing chamber;

a lens situated between the optical transmission medium and the window for collimating the light on a wafer in the processing chamber; and said window having an upper surface and a lower surface that are parallel and angled substantially 3–4 degrees with respect to a horizontal thus being configured to preclude light received from the source of light to reflect off the window and back into the transmission medium, thereby preventing interference with light reflected from the interior space of the processing chamber.

28. The apparatus of claim 27 wherein the window is recessed with respect to the top wall of the processing chamber.

29. The apparatus of claim 28 wherein gas is directed from a recessed portion of the top wall.

30. A method comprising:

providing a semiconductor processing chamber including an interior space enclosed by a plurality of walls with a window mounted on a top one of the walls of the processing chamber;

providing a source of light and an analysis mechanism;

positioning an optical transmission medium between the source of light and the analysis mechanism and the window for directing light into the processing chamber and analyzing the interior space of the processing chamber;

situating a lens between the optical transmission medium and the window for collimating the light on a wafer in the processing chamber; and configuring the window to have an upper surface and a lower surface that are parallel and angled substantially 3–4 degrees with respect to a horizontal in order to reflect the light received from the optical transmission medium so as to not interfere with light reflected from the interior space of the processing chamber.

31. The method of claim 30 wherein the window is recessed with respect to the top wall of the processing chamber.

32. The method of claim 31 wherein gas is directed from a recessed portion of the top wall.

* * * * *